United States Patent
Novak et al.

(10) Patent No.: US 7,442,168 B2
(45) Date of Patent: Oct. 28, 2008

(54) HIGH EFFICIENCY MEDICAL TRANSDUCER WITH ERGONOMIC SHAPE AND METHOD OF MANUFACTURE

(75) Inventors: Theodore A. D. Novak, Northport, NY (US); Alexander L. Darian, Huntington Station, NJ (US); Dan Voic, Clifton, NJ (US); Scott Isola, Deer Park, NY (US); Ronald R. Manna, Valley Stream, NY (US)

(73) Assignee: Misonix, Incorporated, Farmingdale, NY (US)

( * ) Notice: Subject to any disclaimer, the term of this patent is extended or adjusted under 35 U.S.C. 154(b) by 769 days.

(21) Appl. No.: 10/404,374

(22) Filed: Apr. 1, 2003

(65) Prior Publication Data

US 2004/0006269 A1 Jan. 8, 2004

Related U.S. Application Data

(60) Provisional application No. 60/370,364, filed on Apr. 5, 2002.

(51) Int. Cl.
  *A61B 8/00* (2006.01)
  *A61B 8/12* (2006.01)
  *A61B 8/14* (2006.01)
  *A61H 1/00* (2006.01)
  *A61H 1/02* (2006.01)
  *A61H 5/00* (2006.01)
  *H01L 41/00* (2006.01)
  *H02N 2/00* (2006.01)

(52) U.S. Cl. .................. 600/459; 600/437; 600/439; 601/2; 310/311

(58) Field of Classification Search ................ 600/437, 600/459
See application file for complete search history.

(56) References Cited

U.S. PATENT DOCUMENTS

| 4,169,984 A | * | 10/1979 | Parisi .................... 310/323.18 |
| 4,526,571 A | * | 7/1985 | Wuchinich .................. 604/22 |
| 4,634,419 A | | 1/1987 | Kreizman et al. |
| 4,741,731 A | * | 5/1988 | Starck et al. .................. 604/22 |
| 5,312,329 A | * | 5/1994 | Beaty et al. .................... 604/22 |
| 5,371,429 A | * | 12/1994 | Manna ....................... 310/328 |
| 5,397,293 A | | 3/1995 | Alliger |
| 5,449,370 A | * | 9/1995 | Vaitekunas .................. 606/169 |
| 5,480,379 A | * | 1/1996 | La Rosa ...................... 604/22 |
| 5,628,743 A | * | 5/1997 | Cimino ......................... 606/1 |
| 5,810,859 A | * | 9/1998 | DiMatteo et al. ............ 606/169 |
| 5,989,275 A | | 11/1999 | Estabrook et al. |
| 6,051,010 A | | 4/2000 | DiMatteo |
| 6,063,098 A | * | 5/2000 | Houser et al. ............... 606/169 |

* cited by examiner

*Primary Examiner*—Brian L. Casler
*Assistant Examiner*—James Kish
(74) *Attorney, Agent, or Firm*—R. Neil Sudol; Henry D. Coleman; William J. Sapone

(57) ABSTRACT

A tranducer assembly for an ultrasonic surgical instrument includes a front driver having an elongate shaft in one direction and a stud extending in an opposite direction. An electromechanical transducer element is disposed around the stud. The transducer assembly also comprises a rear driver disposed around the stud on a side of the electromechanical transducer element opposite the front driver, the electromechanical transducer element being clamped between the front driver and the rear driver. An inertial or damping mass is fixedly connected to the stud at a point spaced from the rear driver. The stud is of length and thinness to act as a flexible vibration damping element.

17 Claims, 5 Drawing Sheets

US 7,442,168 B2

HIGH EFFICIENCY MEDICAL TRANSDUCER WITH ERGONOMIC SHAPE AND METHOD OF MANUFACTURE

BACKGROUND OF THE INVENTION

This invention relates to a high efficiency medical surgical transducer with an ergonomically enhanced shape. More particularly, this invention relates to a device that will transform electrical signals to mechanical vibrations to allow for ablation of tumors and other unwanted body tissues while allowing line of sight visualization of the operative sight by the surgeon.

Over the past 30 years, several ultrasonic tools have been invented which can be used to ablate or cut tissue in surgery. Such devices are disclosed by Wuchinich et al. in U.S. Pat. No. 4,223,676 and Idemoto et al in U.S. Pat. No. 5,188,102.

In practice, these surgical devices include a blunt tip hollow probe that vibrates at frequencies between 20 kc and 100 kc, with amplitudes up to 300 microns or more. Such devices ablate tissue by either producing cavitation bubbles which implode and disrupt cells, tissue compression and relaxation stresses (sometimes called the jackhammer effect) or by other forces such as micro streaming of bubbles in the tissue matrix. The effect is that the tissue becomes liquefied and separated. It then becomes emulsified with the irrigant solution. The resulting emulsion is then aspirated from the site. Bulk excision of tissue is possible by applying the energy around and under unwanted tumors to separate it from the surrounding structure. The surgeon can then lift the tissue out using common tools such as forceps.

The probe or tube is excited by a transducer of either the piezoelectric or magnetostrictive type that transforms an alternating electrical signal within the frequencies indicated into a longitudinal or transverse vibration. When the probe is attached to the transducer, the two become a single element with series and parallel resonances. The designer will try to tailor the mechanical and electrical characteristics of these elements to provide the proper frequency of operation. Most of the time, the elements will have a long axis that is straight, as shown in FIG. 1. This is done for simplicity and economic considerations. In almost all applications, whether medical or industrial, such an embodiment is practical and useful. However, in applications such as open field brain surgery, such an embodiment is impractical since the doctor is using a microscope while operating, to enlarge the view of the delicate structures of the brain. Here, the length of the transducer/horn combination may be disadvantageous, since the proximal end of the transducer will contact the microscope head and interfere with the ability of the surgeon to manipulate the tool for maximum efficacy. As important, the transducer housing major diameter interferes with the surgeon's field of view of the operative site.

In the past, several inventors have attempted to solve the problem by kinking or bending the transducer or probe element to provide an angled handpiece. With this method, the surgeon handles the distal end of the combination normally while the transducer lies along his or her hand, away from the microscope head and thereby increasing the ability to visualize the operative field. FIG. 2 shows an ultrasonic transducer and probe assembly with a kink or a bend in the front driver of the transducer assembly.

Several factors have limited the benefit of a bent transducer or probe. One is the fact that the bend introduces a vector force that manifests itself as a transverse or bending wave motion. This motion reduces the efficiency of the tip action and increases the energy loss in the transducer itself. As a result, the transducer temperature rises, causing the surface to become too hot to touch. Also, the transverse vibrations lead to large stresses in the vibratory elements which at higher amplitudes cause metal fatigue and probe fracture. The transverse vector increases in direct proportion to the angle of curvature. Because of these design problems, the designer will both limit the bend angle as well as reduce the maximum tip amplitude at which the device will be allowed to vibrate. As an example, one commercially available device gives a maximum amplitude for a straight transducer probe combination as 355 microns while offering a transducer with a 10° angle for the same purpose at only 183 microns, or almost 50% less. Both remedies reduce the efficacy of the operative procedure in that the harder, denser tumors require higher amplitudes and more power to ablate and remove. In addition, the small bend angle still allows the transducer proximal end to contact the microscopes in practice.

The diameter of the transducer body is also a factor in the ergonomics of the device. The larger the unit, the heavier and more difficult it is to manipulate. When poled, most surgeons requested a device that is the size of a large writing pen. Since the electrical power required to ablate tissue and overcome the electromechanical losses in the handpiece is up to 70 watts, making a thinner handpiece that does not get hot during use is problematic due to the fact the crystal mass in a piezoelectric handpiece is reduced. The power density will then rise, increasing power loss and waste heat generation. Similar problems exist for magnetostrictive devices, although these can generally be thinner for given wattage output. However, since magnetostrictive devices cannot easily accommodate a central aspiration port (one that is concentric with the long axis) tissue blockage can occur when aspirating tissue. This is a major detriment.

Other factors, which are desirable in a practical embodiment, would be a fluid passageway with no joints within the transducer case to prevent liquid leakage into the interior of the transducer that would cause failure of the electrical components. In addition, the case of the unit should be isolated from the vibrations of the probe and transducer itself. If the case vibrated in sympathy with the transducer, the surgeon would feel the vibrations in his or her hand. This leads to less tactile feedback during the operation, fatigue and could in fact lead to damage of the hand upon long exposure.

OBJECTS OF THE INVENTION

An object of the present invention is to provide an improved ultrasonic surgical instrument which may be used in conjunction with microscopes.

Another, more specific object of the present invention is to provide an improved ultrasonic surgical instrument with a piezoelectric transducer which has an effective angle of curvature greater than 10°.

It is a further object of the present invention to provide an improved ultrasonic surgical instrument with concentric flow through a center of a handpiece and with no internal fluid passage joints which may leak and cause product failure.

Yet a further object of the present invention is to provide an improved ultrasonic surgical instrument with isolation of the tool vibrations from the transducer case.

An additional object of the present invention is to provide an improved ultrasonic surgical instrument which has a handpiece with a diameter of less than about one inch.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

A transducer assembly for an ultrasonic surgical instrument comprises, in accordance with the present invention, a front driver having an elongate shaft extending in one direction and a stud extending in an opposite direction. An electromechanical transducer element (for instance, a plurality of piezoelectric crystal disks) is disposed around the stud. The transducer assembly also comprises a rear driver disposed around the stud on a side of the electromechanical transducer element opposite the front driver, the electromechanical transducer element being clamped between the front driver and the rear driver. An inertial or damping mass is fixedly connected to the stud at a point spaced from the rear driver.

Pursuant to a specific feature of the present invention, the inertial or damping mass is an end cap of a transducer case. However, it is alternatively possible for the inertial or damping mass to be located inside a case, rather than being part of the case. Where the inertial or damping mass is an end cap, it may be connected to a substantially rigid case member in a snap-lock fit.

The fixed interconnection of the stud and the inertial or damping mass may be effectuated as an interference fit of an externally threaded end element of the stud in an internally threaded counter bore in the inertial or damping mass. The inertial or damping mass is preferably torqued onto the threaded end element until an end thereof and an end of the counter bore mate.

Pursuant to a particular feature of the present invention, the stud projects a distance of between 2.50 and 3.25 inches from a front face of the electromechanical transducer. More particularly, the stud projects a distance of between 2.7 and 3.0 inches from the front face of the electromechanical transducer. In addition to a uniquely long length, the stud is formed with an especially thin wall, for instance, with a thickness between approximately 0.010 and 0.25 inch. The thin wall and the length of the stud enable the stud to function as a flexible element in damping vibrations of the electromechanical transducer.

Where the elongate shaft of the front driver is curved at a bend region to form a first portion coaxial with the stud and a second portion at an angle with respect to the stud, the transducer assembly further comprises a first substantially rigid case member disposed about the electromechanical transducer element and the first portion of the elongate shaft, a second substantially rigid case member disposed about the second portion of the elongate shaft, and a flexible coupling member disposed about the elongate shaft at the bend region. The flexible coupling member is connected on one side to the first substantially rigid case member and on an opposite side to the second substantially rigid case member.

According to a further feature of the invention, a splined ring is disposed between the second substantially rigid case member and the second portion of the shaft. Where the second portion of the elongate shaft is formed with an enlarged amplification mass, the splined ring is disposed in engagement with the mass.

According to yet another feature of the present invention, the first substantially rigid case member is provided with a barb or port element and a vent hole. The vent hole is spaced in a proximal direction from the barb or port element and is located on a same side of the first substantially rigid case member as the barb or port element.

A method of manufacturing a transducer for an ultrasonic medical device utilizes a front driver with a rearwardly extending stud having an externally threaded free end. A threaded counter bore is formed in a damping mass so that internal threads of the counter bore terminate a predetermined distance from a bottom of the counter bore. The damping mass is threaded onto the threaded free end of the stud until the stud threads bottom. The damping mass is subjected then to an additional torque until the stud free end and a counter bore end mate.

DETAILED DESCRIPTION OF THE PREFERRED EMBODIMENTS

A piezoelectric transducer is disclosed herein which incorporates a plurality of features which in concert exhibit features desirable in the performance of delicate medical operations. In addition, the various features may have utility in and of themselves in different applications. The terminology used in discussing the transducer, an associated instrument assembly, and a method of manufacture will be that generally accepted in the art of ultrasound engineering. The term "fixedly connected" when used herein to describe the coupling of a stud to an inertial or damping mass refers to a connection which is such that the stud and the inertial or damping mass were fabricated as a single or unitary object. Thus, the connection is rigid and essentially irreversible.

Figure 1:
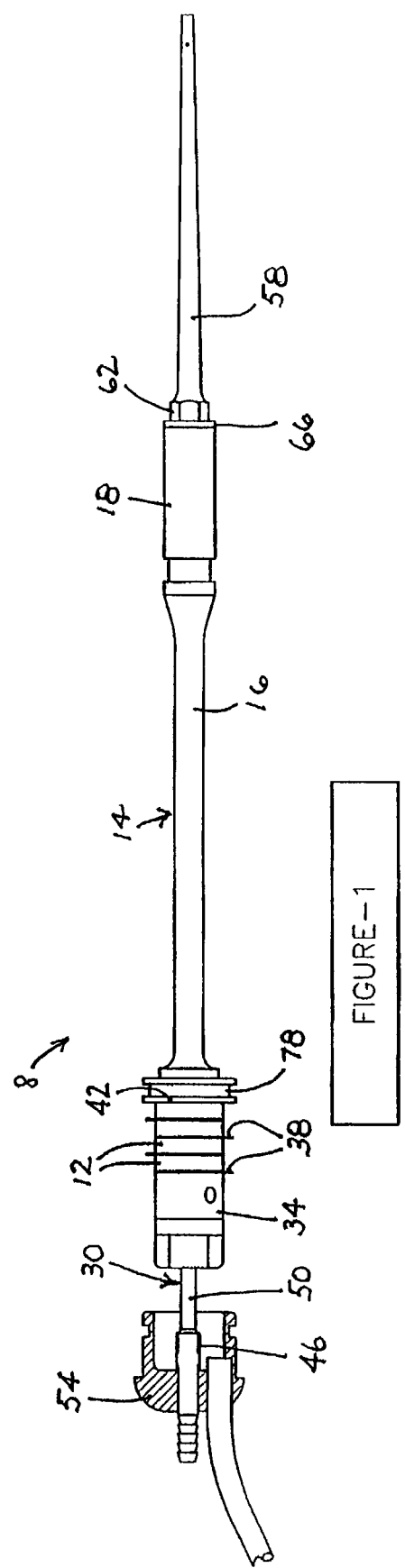
FIG. 1 is partially a side elevational view and partially a cross-sectional view of a transducer in accordance with the present invention, showing an attached ultrasonic horn or probe.
Figure 2:
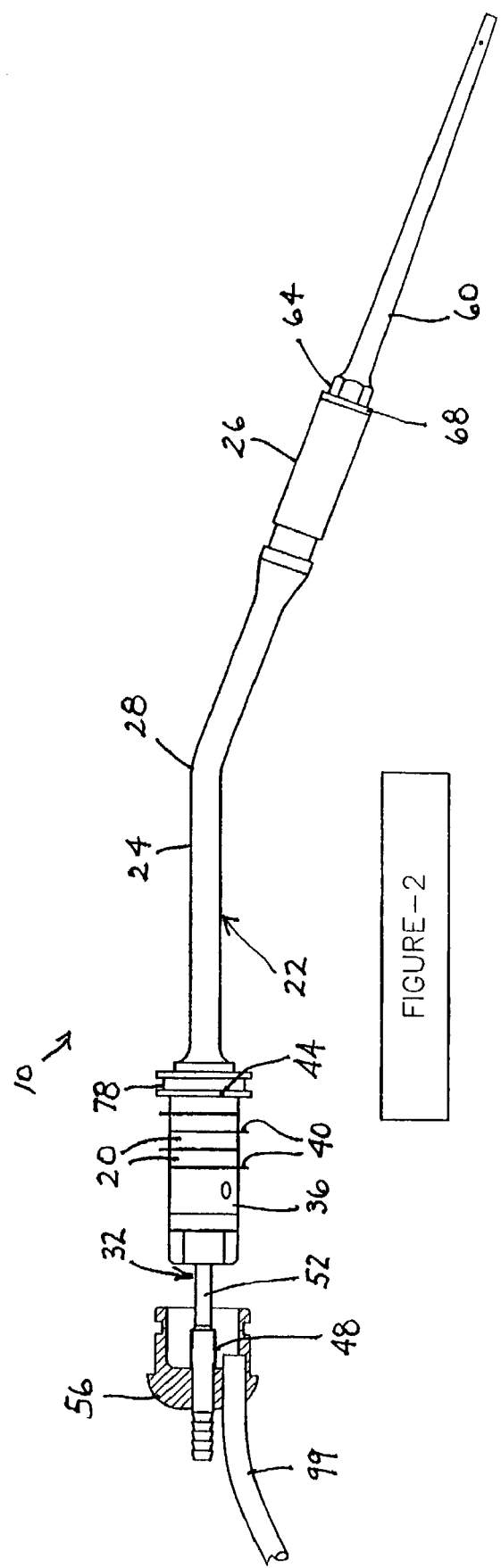
FIG. 2 is partially a side elevational view and partially a cross-sectional view of another transducer in accordance with the present invention, showing an attached horn or probe.

FIG. 1 shows a piezoelectric transducer 8 in a straight or unbent form, while FIG. 2 shows another transducer 10 in an angled or bent form. The transducer of FIG. 1 includes a stack of piezoelectric crystals 12 having a front driver 14 consisting in part of a rod 16 and a transformer mass 18 for amplifying the longitudinal motion generated by the piezoelectric crystals 12. The transducer of FIG. 2 likewise comprises a stack of piezoelectric crystals 20 and a front driver 22 including a rod or shaft 24 and a motion-amplification mass 26. Rod or shaft 24 is formed with a bend 28.

Front drivers 14 and 22 are constructed of materials with high acoustic efficiency such as titanium, although other materials might be envisioned. Each driver 14 and 22 is hollow in that a bore (not shown) is provided throughout which will become the aspirant passageway when the unit is fully assembled. The crystals 12 and 20 are of man made materials such as Lead Zirconate Titanate (PZT) composites shaped into a ring configuration.

Crystals 12 surround a hollow stud 30 which projects rearwardly, i.e., in a proximal direction, from front driver 14, while crystals 20 surround a hollow stud 32 which projects in a rearward or proximal direction from front driver 22. Transducers 8 and 10 further include respective rear drivers 34 and 36 each of which is a two piece construction of tungsten and titanium. Each transducer device 8 and 10 is configured as a Langevin Sandwich type transducer wherein the crystals 12 or 20 with electrodes 38 or 40 are subjected to compression by tightening the rear driver 34 or 36 via internal threads to the stud 30 or 32 of front driver 14 or 22 at a predetermined torque or prestress level. By connecting the electrodes 38 or 40 electrically in parallel, the transducer 8 or 10 may be set to vibrate when an alternating signal is applied to the positive and negative connections. These features are well known to the art.

An improvement over prior art is that studs 30 and 32 of front drivers 14 and 22 are each elongated, for instance, to a length of 2.888 inch ±0.100 inch, from a crystal distal face 42, 44 and terminate at the proximal end in a respective threaded element 46, 48 which has thread of the same size of that of the respective rear driver 34, 36, to allow assembly of the crystal section. Studs 30 and 32 have shanks 50 and 52 of reduced wall thickness to provide decoupling of the vibrations from the respective crystal stack 12 and 20 to a rear element, for instance, a casing end cap. By reducing the wall thickness of stud shank 50, 52 to a point which allows the unit to flex in compression and tension, the vibration of the respective rear driver 34, 36 will be isolated from the balance of the assembly. In order to provide decoupling, studs 30, 32 are threaded and sealed into a respective rear damping mass 54, 56 that because of materials used (stainless steel, titanium tungsten) and the volume provided has a relatively significant inertia that dampens any vibrations resulting from the transducer 8, 10 and prevents transmission to the case and liquid passageway. The threaded element 46, 48 at the proximal end of the stud 30, 32 must mate to the female thread of the inertial or damping mass 54, 56 in a tight, interference fit. In practice it has been found that the damping mass 54, 56 must be counter bored to accept the internal threads. The internal threads must terminate a certain distance, for instance, approximately 0.062 inch, from the bottom of the counter bore, depending on the size and power of the transducer, as well as on the characteristic operating frequency. The damping mass 54, 56 is threaded onto the threaded element 46, 48 until the stud threads bottom. Then the damping mass 54, 56 is subjected to an additional torque until the stud end and the counter bore ends mate. In this way, a fluid tight passageway is formed and the metal parts act as a single piece. Any other means such as a lower torque or sealants do not provide the coupling required to eliminate transverse vibrations and early transducer failure.

Each front driver 14, 22 is connected at a distal side of the respective motion-amplification mass or gain stage 18, 26 to a horn or probe 58, 60. The overall length of the assembly of transducer 8, 10 and probe 58, 60 corresponds to one full wavelength of the desired operating frequency, although integer multiples of the half wavelength greater than or equal to two (one full wave) could be envisioned. Probe 58, 60 is connected to transducer 8, 10 and particular motion-amplification mass 18, 26 via a nut 62, 64 and a washer 66, 68 at a frequency node point, as is the current state of the art for ultrasonic neuro-aspirators of this type. It can be envisioned that with redesign of the probe 58, 60, the connection could be made at an antinode as well. In addition to the motion amplification provided by mass or gain stage 18, 26, probe 58, 60 provides a gain such that the distal tip amplitudes approach 400 microns.

Bend 28 of transducer 10 is 2.46 inches from the crystal stack distal face 44. This dimension depends upon the gain ratio of front driver 22 and may vary for different diameters and frequencies. The radius of curvature of rod 24 at bend 28 is ½"0 which again was found to be fairly sensitive. If the bend radius is 1 inch, for instance, significant transverse vibrations were present at the rear mass. Smaller radii stressed the metal to the point of tearing or fracture. When constructed in this form, transducer 10 provided an angle of curvature of 20°.

The diameter of front driver rod or shaft 24 has been found to be optimal between 0.230 inch maximum and 0.205 inch minimum in order for the shaft to provide isolation for longitudinal as well as transverse vibrations to the rear case. Where rear inertial mass 56 is shaped to act as a rear cover for a transducer case 70 (FIG. 3), a plastic housing member 72 of the transducer case may be placed over the distal end of the transducer 10 until its proximal end mates to a locating boss 74 (FIGS. 2-4) of inertial mass 56. By sealing the interface with known means such as O-rings 76 or a sealant, a gas tight and liquid tight seal is made which allows the unit to be autoclaved. A front nodal ring 78 of the transducer 10 is likewise sealed by an O-ring 79. Case 70 so formed can be grasped and manipulated by a surgeon to project the tip of the probe 60 against unwanted tissue at a surgical site in a patient. Since the case 70 only touches the rear inertial mass 56 and the front nodal ring 78 of the transducer 10, no vibrations are coupled to the case itself, fulfilling one on the important elements of the design.

Figure 5:
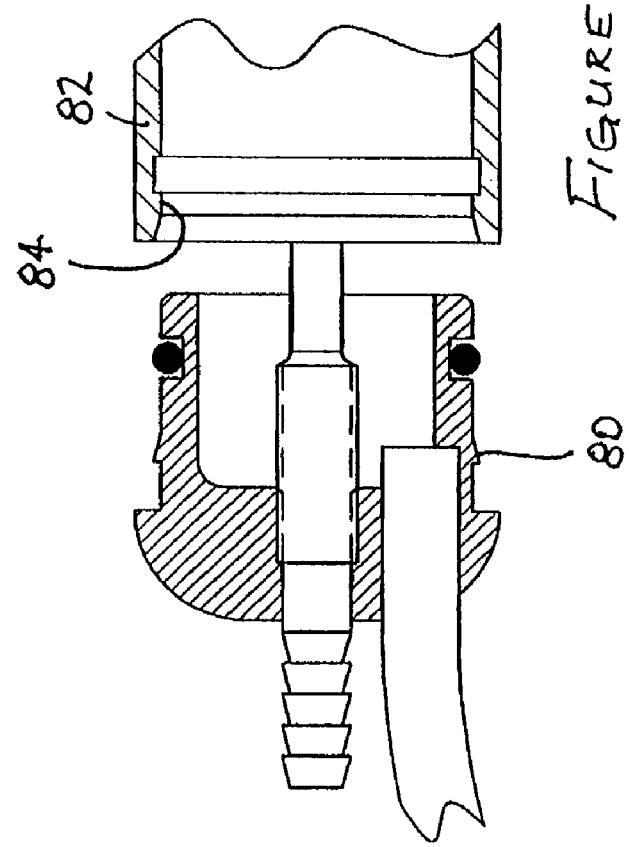
FIG. 5 is a cross-sectional view, on the scale of FIG. 4, of an alternative end cap in accordance with the present invention, showing the end cap in an exploded or disassembled configuration relative to a case member.
Figure 6:
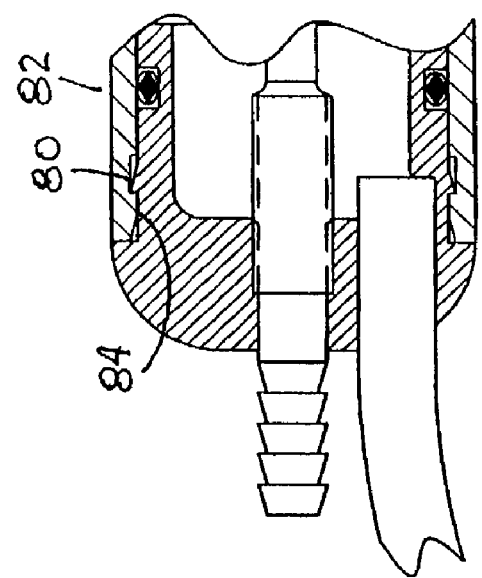
FIG. 6 is a cross-sectional view of the end cap of FIG. 5 in an assembled configuration.

One modification which provides ease of assembly as well as reduction of parts count since fasteners are not needed is a snap fit assembly. Here rear inertial mass 54, 56 includes a ramped ridge 80, as illustrated in FIGS. 5 and 6. An inner surface of a plastic or polymeric case member 82 has a corresponding internal protrusion 84. When the case member 82 is slid over the rear inertial mass 56, the case protrusion 84 contacts the ramped or inclined side (not separately labeled) of the ridge 80. As more force is applied, the plastic case member 82 expands slightly to allow the protrusion 84 to snap over the ramped ridge 80. Since the proximal side (not separately labeled) of the ridge 80 is perpendicular to the boss 74, the case member 82 is effectively trapped. If sealant or O-rings are provided the assembly is essentially complete without the need for locking rings, screws or other fastening means.

In constructing the embodiment, several other inventions of note were developed to complete the assembly.

In all surgical aspirators of this type, liquid must be supplied to the operating site. This liquid is generally sterile saline but this is not critical to the invention. The liquid serves to cool the probe, provide irrigation and cooling of the tissues and provides a liquid into which the tissue may be disrupted, emulsified and subsequently aspirated. In several prior art designs, the necessary fluid pathway is provided by a sheath made of silicone or another elastomer, which surrounds the probe and provides a coaxial pathway for the fluid.

Figure 3:
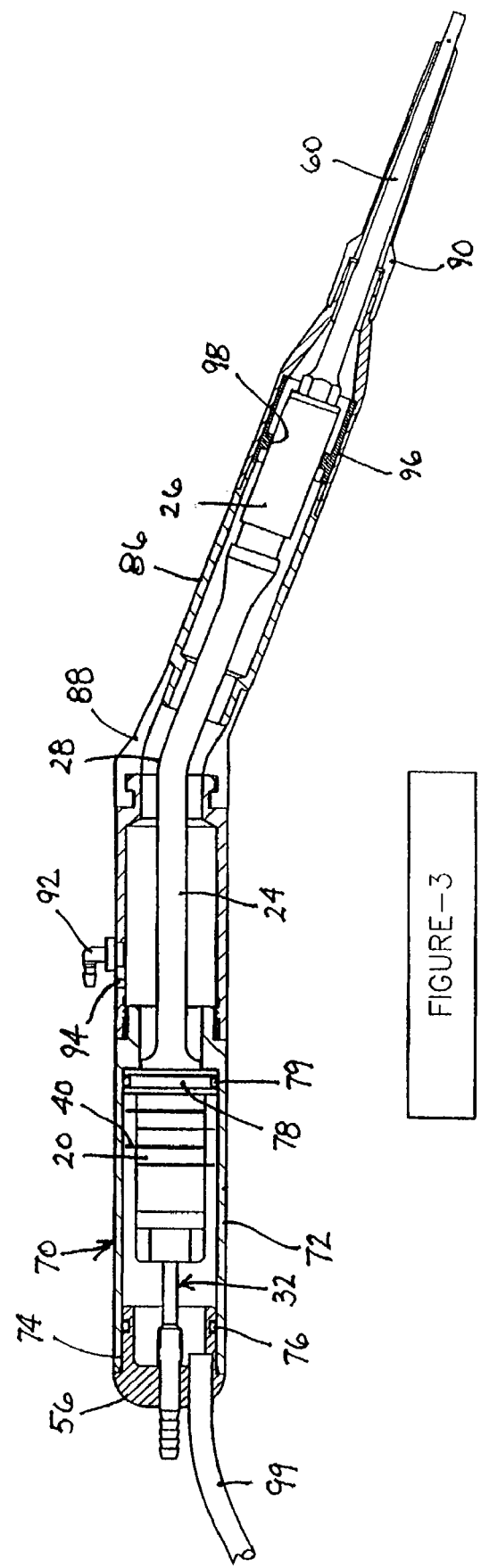
FIG. 3 is a side elevational view of the transducer and probe of FIG. 2 and a cross-sectional view of a casing and sheath assembly in accordance with the present invention.
Figure 4:
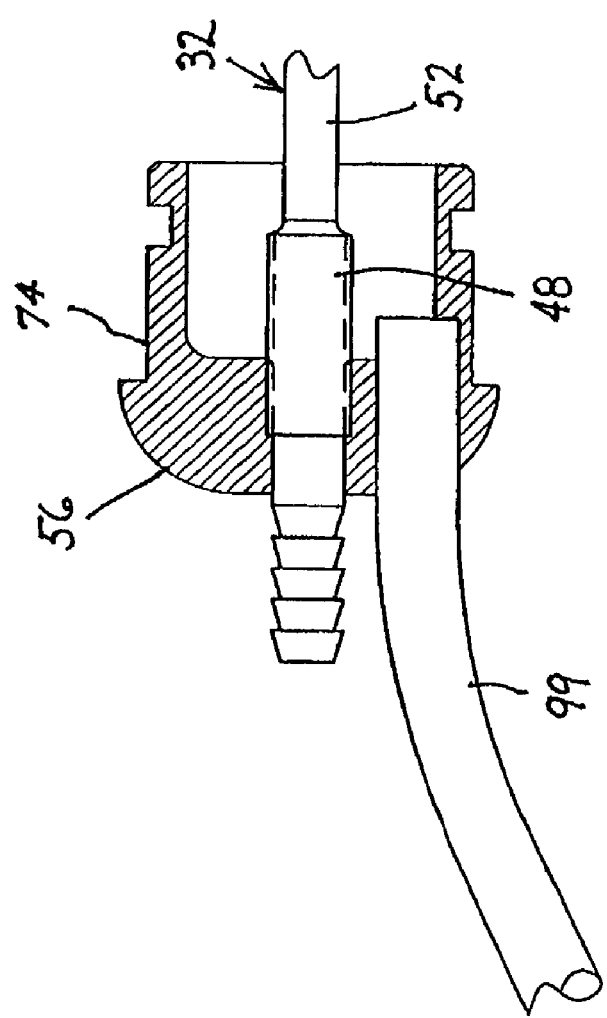
FIG. 4 is a cross-sectional view, on a larger scale, of an inertial mass end cap with couplings shown in FIGS. 2 and 3, in accordance with the present invention.

As depicted in FIG. 3, case 70 of the present surgical instrument assembly includes housing member 72 and another hard polymeric case member 73. Housing member 72 and case member 73 are rigidly connected to one another and may be considered a single rigid case member. As further depicted in FIG. 3, case 70 additionally includes a hard plastic case extender or sheath 86 which mates to the transducer case member 73, 82 via a flexible connector or coupling 88. This allows the hard plastic sheath 86 to be placed over the probe 60 (after attaching to the transducer 10 via a threaded joint) and snapped onto the case members 70, 82 providing a liquid tight seal. This is an improvement over prior art which required a one piece banana shaped plastic case which was a clam shell configuration and was difficult to seal and make robust against damage from handling and dropping. The flexible coupling 88 and sheath 86 thus provide significant benefits.

A silicon flue 90 is then placed over the probe 60 and snapped onto the distal end of the plastic extender 86 in a standard manner. The entire assembly constitutes an improvement over prior art in that a long silicone sheath has been used in the past. When the surgeon grasped the flexible sheath, ultrasonic energy could be coupled to the hand, inducing discomfort.

A fluid barb or port element 92 (FIG. 3) is placed into the transducer case members 70, 82 near its distal end. The barb 92 communicates with the interior of the case members 70, 82. When a flexible liquid tube (not shown) is placed onto the barb 92, liquid may be pumped into the interior cavity formed by the case members 70, 82 and the front driver nodal ring 78. Liquid will then be forced to travel distally through the annular passageway formed by the transducer front driver 22, the transducer case members 70, 82, the probe 60 and the silicon flue 90. The only outlet then is the proximal end of the flue 90 that is in close proximity to the probe distal end. The liquid will then flood the area around the probe and provide the advantages described herein.

Further improvement is the inclusion of a vent hole 94 spaced proximally from the fluid barb 92. This vent hole 94 allows air to flow into the interior space of case member 70, 82. It was found that when this vent is not provided, fluid is held in the cavity when the pump stops running, due to a vacuum being developed above the liquid level, similar to that of a gravity type water cooler. With the bleed hole provided, the vacuum is relieved and liquid flows due to gravity. The benefit is that the liquid does not back up into the area around the nodal ring which, if left there, increases the load on the system and consequently reduces the efficiency of the device. It also leads to premature product failure since the cavitation erosion caused by the ultrasonic energy in such fluid wears the metal away. For the reasons given, the vent hole should be located at the top of the transducer, as shown in FIG. 3.

As illustrated in FIG. 3, a splined ring 96 is provided that serves to locate the hard sheath 86 concentrically around the front driver 22. This ring 96 is made from a hard elastomer or polytetrafluorethylene which is pressed into sheath 86 or is otherwise fixedly located within it by known means. The ring 96 not only keeps the sheath 86 concentric with the front driver 22, it was found to suppress the transverse vibrations throughout the assembly. Splines 98 of ring 96 allow for liquid passage down to the distal end. In practice the internal diameter of the ring 96 is a sliding fit against the front driver 22.

In one example of transducer 10 (FIG. 3) described herein, damping mass 56 is 13 grams (0.46 ounce), shank 52 of stud 34 has a wall thickness of 0.017 inch and inner and outer diameters of 0.078 inch and 0.112 inch, respectively, rod or shaft 24 has a diameter of 0.215 inch, and the design operating frequency is about 23 kHz. This transducer has been shown to be an effective tool when used to ablate unwanted tissue within the body. The efficiency of the transducer is very high in that it can provide over 70 watts of power for extended periods without a significant temperature rise while providing 400 microns or more at the tips distal end. The overall diameter is 0.800". In all, it effectively provides all of the desired features for a device of this type. For example, as an indication of how the design suppresses transverse vibrations, the feeding of liquid is not necessary to reduce vibrations. The instrument may be operated without liquid until heat generated at the joint between front driver 22 and probe 60 requires the liquid for cooling purposes.

Reference designation 99 in FIGS. 3-6 represents an electrical cable. Individual cable wires (not illustrated) are connected to electrodes 40.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for instance, that the inertial mass to which the proximally extending transducer stud is connected need not be an end cap of the transducer casing. Instead, the inertial mass may be a separate element located distally of the proximal end cap of the casing. In addition, the coupling of the proximal ends of studs 30, 32 to inertial or damping mass 54, 56 may be accomplished by other means such as welding, which ensures that the studs and the damping mass cofunction as an integral or unitary piece. Accordingly, it is to be understood that the drawings and descriptions herein are proffered by way of example to facilitate comprehension of the invention and should not be construed to limit the scope thereof.

What is claimed is:

1. A transducer assembly for an ultrasonic surgical instrument, comprising:
   a front driver having an elongate shaft extending in one direction and a stud extending in an opposite direction;
   an electromechanical transducer element disposed around said stud;
   a rear driver disposed around said stud on a side of said electromechanical transducer element opposite said front driver, said electromechanical transducer element being clamped between said front driver and said rear driver; and
   an inertial or damping mass fixedly connected to said stud at a point spaced from said rear driver.

2. The transducer assembly of claim 1 wherein said inertial or damping mass is an end cap of a transducer case.

3. The transducer assembly of claim 2 wherein said casing includes a substantially rigid case member locked to said end cap in a snap-lock fit.

4. The transducer assembly of claim 1 wherein said stud is provided with an externally threaded end element, said inertial or damping mass being provided with an internally threaded counter bore, said threaded end element being inserted into said counter bore in an interference fit.

5. The transducer assembly of claim 4 wherein said inertial or damping mass is torqued onto said threaded end element until an end thereof and an end of said counter bore mate.

6. The transducer assembly of claim 1 wherein said stud projects a distance of between 2.50 and 3.25 inches from a front face of said electromechanical transducer.

7. The transducer assembly of claim 6 wherein said stud projects a distance of between 2.7 and 3.0 inches from said front face of said electromechanical transducer.

8. The transducer assembly of claim 1 wherein said stud has a wall of a thickness sufficiently small to enable said stud to function as a flexible element in damping vibrations of said electromechanical transducer.

9. The transducer assembly of claim 8 wherein said stud has a wall thickness between approximately 0.010 and 0.25 inch.

10. The transducer assembly of claim 1 wherein said elongate shaft of said front driver is curved at a bend region to form a first portion coaxial with said stud and a second portion at an angle with respect to said stud, said first portion and said second portion being substantially rigid with one another, further comprising:
- a first substantially rigid case member disposed about said electromechanical transducer element and said first portion of said elongate shaft;
- a second substantially rigid case member disposed about said second portion of said elongate shaft; and
- a flexible coupling member disposed about said elongate shaft at said bend region, said flexible coupling member being connected on one side to said first substantially rigid case member and on an opposite side to said second substantially rigid case member.

11. The transducer assembly of claim 10 wherein a splined ring is disposed between said second substantially rigid case member and said second portion of said shaft.

12. The transducer assembly of claim 11 wherein said second portion of said elongate shaft is formed with an enlarged amplification mass, said splined ring being disposed in engagement with said mass.

13. The transducer assembly of claim 10 wherein said first substantially rigid case member is provided with a barb or port element and a vent hole.

14. The transducer assembly of claim 13 wherein said vent hole is spaced in a proximal direction from said barb or port element and is located on a same side of said first substantially rigid case member as said barb or port element.

15. A handpiece for an ultrasonic surgical instrument, comprising:
- a transducer assembly including a front driver having an elongate shaft, said shaft being curved at a bend region to form a first portion and a second portion extending at an angle with respect to one another, said first portion and said second portion being substantially rigid with one another; and
- a casing including a first substantially rigid case member, a second substantially rigid case member and a flexible coupling member, said first substantially rigid case member being disposed about said first portion of said shaft, said second substantially rigid case member being disposed about said second portion of said shaft, said flexible coupling member being disposed about said elongate shaft at said bend region, said flexible coupling member being connected on one side to said first substantially rigid case member and on an opposite side to said second substantially rigid case member, said front driver including a stud projecting in a direction opposite said shaft, said stud being rigidly connected to an inertial or damping mass.

16. The handpiece of claim 15 wherein said transducer assembly includes an electromagnetic transducer element, said stud extending a substantial distance from a front face of said electromechanical transducer element.

17. The handpiece of claim 15 wherein said inertial or damping mass is formed as an end cap to said first substantially rigid case member.

\* \* \* \* \*